United States Patent [19]

Arnold et al.

[11] Patent Number: 5,283,339

[45] Date of Patent: Feb. 1, 1994

[54] IMMOBILIZED METAL AQUEOUS TWO-PHASE EXTRACTION AND PRECIPITATION

[75] Inventors: Frances H. Arnold; Gerald E. Wuenschell, both of Pasadena, Calif.

[73] Assignee: California Institute of Technology, Pasadena, Calif.

[21] Appl. No.: 925,906

[22] Filed: Aug. 5, 1992

Related U.S. Application Data

[63] Continuation of Ser. No. 598,051, Oct. 15, 1990, abandoned, which is a continuation-in-part of Ser. No. 275,586, Nov. 23, 1988, abandoned.

[51] Int. Cl.$^5$ .................. C07F 1/08; C07F 3/00; C07F 15/00
[52] U.S. Cl. .................. 548/104; 548/108; 548/403; 556/114; 556/134; 556/148; 562/448; 562/557; 562/564; 562/568; 562/571; 562/575; 564/505
[58] Field of Search .......... 556/114, 134, 148; 562/448, 557, 564, 568, 571, 575; 564/505; 548/104, 108, 403

[56] References Cited

U.S. PATENT DOCUMENTS

| | | | |
|---|---|---|---|
| 2,709,178 | 5/1955 | Schlapter | 562/564 |
| 2,819,301 | 1/1958 | Monson et al. | 260/518 |
| 4,247,301 | 1/1981 | Honnen | 44/63 |
| 4,330,677 | 5/1982 | Linke et al. | 562/583 |
| 4,760,176 | 7/1988 | Halpern et al. | 562/564 |

OTHER PUBLICATIONS

Buckmann, Andreas F. et al. "Preparation of Technical Grade Polyethylene Glycol (PEG) ($M_r$ 20,000)-$N^6$-(-2-Aminoethyl)-NADH by a Procedure Adaptable to Large-Scale Synthesis", Biotechnology and Applied Biochemistry, vol. 9, pp. 258-268 (1987).

Dust, Julian M. et al. "Proton NMR Characterization of Poly(ethylene glycols) and Derivatives", Macromolecules, vol. 23, pp. 3742-3746 (1990).

Van Dam, Mariana E. et al. "Metal Affinity Precipitation of Proteins", Biotechnology and Applied Biochemistry, vol. 11, pp. 492-502 (1989).

Jigarjian, J. Org. Chem., 21, pp. 90-92 (1956).

*Primary Examiner*—Paul J. Killos
*Assistant Examiner*—Porfirio Nazario
*Attorney, Agent, or Firm*—Poms, Smith, Lande & Rose

[57] ABSTRACT

Metallated compounds can be used to extract or precipitate proteins from solution. The compounds can be polymers, such as polyalkylene glycols, which can be mono- or bimetallated or smaller bis-metal chelates, such as ethylenebis(oxyethylenenitrilo)tetraacetic acid. The monometallated polymers are preferred in the extraction process whereas the bimetallated compounds are preferred in the precipitation process. In addition, new PEG compounds which are capable of chelating a variety of metals are described. Both mono- and bimetallated forms are set forth. The new metallated compounds are very effective in extracting or precipitating proteins from solution.

9 Claims, No Drawings

IMMOBILIZED METAL AQUEOUS TWO-PHASE EXTRACTION AND PRECIPITATION

RELATED APPLICATION

This is a continuation of copending application Ser. No. 07/598,051 filed on Oct. 15, 1990 now abandoned. which is a continuation-in-part application of our copending application Ser. No. 07/275,586, filed Nov. 23, 1988, now abandoned.

TECHNICAL FIELD

This invention relates to processes for the selective isolation of proteins by extraction with metal-chelating polymers and precipitation with metal-chelating polymers or bis-metal chelates. In particular, the extraction process of the present invention employs an aqueous multiple-phase system in which one of the phases contains chelated metals. Selected proteins are drawn into this phase by virtue of their interaction with the metal. The precipitation process entails the addition of metal-chelating polymers or bis-metal chelates to protein solutions. Proteins which exhibit affinity for these metals will be selectively precipitated. In addition, the invention also involves novel polyethylene glycol compounds (PEG) that are very useful in these processes.

BACKGROUND ART

The use of multiple-phase aqueous systems for the extraction of proteins has been disclosed in the prior art. Affinity ligands have been used to increase the selectivity of protein partitioning in these systems. For example, the affinity partitioning of phosphofructokinase from fresh baker's yeast in PEG 6000-bound Cibacron blue F3G-A/dextran is reported in *Trends in Biotechnology*, Vol. 2, No. 2, 1984, pp. 31-35, "Large-scale affinity purification—state of the art and future prospects." The article notes the high cost of one of the most frequently used polymers, dextran. Similarly, the large-scale purification of formate dehydrogenase from *C. boidinii* by partitioning with PEG-6000-Procion Red HE3b was reported in "Process Design for Large-Scale Purification of Formate Dehydrogenase from *Candida boidinii* by Affinity Partition," *Journal of Chromatography*, Vol. 376, pp. 375-384, 1986. The feasibility of recycling the PEG-ligand was demonstrated. An enzyme yield of 74% was reported for the largest-scale separation from 220 kg of *Candida boidinii* cells.

In general, the prior art aqueous two-phase extractions that do not employ affinity ligands have resulted in poor selectivity. On the other hand, the prior art systems that used affinity ligands had very specific applicability and could not be applied to a very wide variety of proteins.

Many of the prior art affinity liquid-liquid extraction systems require the use of dextran, which is expensive. While the use of PEG/salt systems would greatly reduce the expense, high salt concentrations disrupt most affinity interactions. High concentrations of certain salts, however, are known to promote metal binding. In the present invention, the interaction between the protein and the metal held by the PEG-chelate is not disrupted by high concentrations of the salts used to form aqueous two-phase systems. These salts include alkali metal and alkaline earth metal citrates, carbonates, silicates, sulfates, formates, succinates, tartrates and phosphates. They are generally used in concentrations between 5 and 15% (w/w) of the total solution for forming two phases. The concentration appropriate for any specific system is determined by the phase diagram of the particular system.

Metals have been immobilized by chelates attached to resins for purification of proteins by chromatography and fixed-bed adsorption. This was first demonstrated in 1975 by Porath (*Nature*, Vol. 258, pp. 598-599). Although U.S. Pat. No. 4,765,834 discloses the use of aqueous multiphase systems for the recovery of metals, metal-chelating polymers have not been used for extraction or precipitation of proteins.

There have been some reports of affinity precipitation of enzymes in the prior art. For example, lactate dehydrogenase and glutamate dehydrogenase have been precipitated with Bis-NAD; *Analytical Biochemistry* 133, pp. 409-416 (1983). Bis-NAD was used to precipitate both lactate dehydrogenase and glutamate dehydrogenase whereas yeast alcohol dehydrogenase required the presence of salt to enhance its precipitation; liver alcohol dehydrogenase did not precipitate. A Procion Blue analog of NAD was used to precipitate rabbit muscle lactate hydrogenase; ibid, 158, 382-389 (1986). Bis-Cibacron Blue has been used to precipitate 90% of lactate dehydrogenase, 50% bovine serum albumin, and 20% chymosin from solution; *Journal of Chromatography*, 376, 157-161 (1986). The ability of salts of metals such as zinc and copper to precipitate proteins is known. None of the prior art descriptions of protein precipitation, however, suggest the use of chelated metals for this purpose.

DISCLOSURE OF THE INVENTION

This invention involves the selective partitioning and/or concentration of proteins present in solution through the use of a multiple-phase aqueous system containing a polymer derivatized so that it chelates metals. A commonly used polymer is poly(ethylene) glycol, usually abbreviated as PEG.

It also involves the selective precipitation of proteins using either polymer-based or nonpolymeric molecules incorporating two or more metallated chelating sites per molecule. Examples are given for protein precipitation utilizing PEG-derived bis-metal chelates as well as the bis-copper complex of a commercially-available nonpolymeric chelate, ethylenebis-(oxyethylenenitrilo)-tetraacetic acid, commonly referred to as EGTA. The ability of these materials to precipitate proteins is indicated by the rapid formation of turbidity in a solution containing the metal chelate and the protein. The precipitate forms upon allowing the solution to stand for several hours.

A molecule containing one, two, or more than two chelation sites will be referred to as a mono-chelate, bis-chelate, or multi-chelate, respectively, if present as the free ligand and as a mono-metal chelate, bis-metal chelate, or multi-metal chelate if metallated.

Both the extraction and precipitation techniques rely on the affinity of particular proteins for particular chelated metal cations. One factor is the metal used. For example, since copper and, to some extent, nickel are known to interact with histidines, these metals would be good choices for separation of proteins that contain accessible histidines. Another factor is the nature of the metal-chelate complex. For instance, if a metal chelate is used that carries a net positive charge, this chelate would be expected to interact more favorably with a protein whose surface metal binding sites are adjacent to regions of net negative charge, rather than with a protein in which those sites are adjacent to regions of neutral or net positive charge.

In addition, we have synthesized new chelating PEG derivatives which can bind metal ions such as $Cu^{2+}$, $Zn^{2+}$, $Ni^{2+}$, $Fe^{3+}$, $Fe^{2+}Co^{2+}$, and $Ca^{2+}$, as well as heavy metals such as Hg and Cd. The metallated derivatives can, in turn, be used in the extraction or precipitation of proteins that interact with these metals.

The new unmetallated compounds correspond to the formula:

A-P-B.

If the compound is a low molecular bis-chelate, for use as a protein precipitation agent, then A=B and represents the metal-chelating portion of the molecule. P is a "bridging group" which separates the chelation sites. This group may be varied depending on the exact properties desired for the precipitating agent. Characteristics considered in choosing this bridging group include:
1. Length of the bridge between the chelation sites.
2. Flexibility of the bridge.
3. Chemical nature of the bridge and the effect this has on the solubility of the precipitating agent and its protein complex.
4. Geometry of the bridge, and the influence such geometry has on the protein binding (including chiral effects).
5. Availability, economy and ease of preparation of the bis-chelate from relevant precursors.

If the compound is polymer-based, P represents the backbone of the polymer. The polymer-based systems currently under consideration correspond to the formula:

A-CH(R)CH$_2$[OCH(R)CH$_2$]$_n$-B.

If R=H, then the compound is a poly(ethylene glycol), or PEG, derivative. If R=CH$_3$, then the compound is a poly(propylene glycol), or PPG, derivative. n is chosen so that the compound has a molecular weight ranging from about 1,500 to about 20,000, depending on the desired properties of the compound. If the compound is a bis-chelate, then A=B. If the compound is a mono-chelate, used for extraction of proteins rather than precipitation, then B=OCH$_3$ or OH. A is the chelating group, i.e. a group which chelates metal ions, examples of which include:
a. —N(CH$_2$COOH)$_2$
b. —NHCH$_2$CH$_2$NHCH$_2$CH$_2$NH$_2$
c. —NHCH$_2$CH$_2$N(CH$_2$CH$_2$NH$_2$)$_2$
d. —NHCH$_2$CH$_2$CH$_2$NHCH$_2$CH$_2$NHCH$_2$CH$_2$CH$_2$NH$_2$
e. —NHCH$_2$CH$_2$NHCH$_2$CH$_2$NHCH$_2$CH$_2$NH$_2$ f. 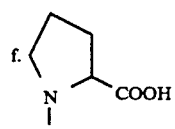

g. —NHCH(X)COOH (D- or L-amino acids)
h. —N(CH$_2$COOH)CH(X)COOH[D- or L-N-(carboxymethyl)amino acids]; wherein X is g and h is —H; —CH$_3$; —CH(CH$_3$)$_2$; —CH$_2$CH(CH$_3$)$_2$; —CH(CH$_3$)CH$_2$CH$_3$; —CH$_2$CH$_2$SCH$_3$; —CH$_2$OH; —CH(OH)CH$_3$; —CH$_2$SH; —CH$_2$COOH; —CH$_2$CONH$_2$; —CH$_2$CH$_2$COOH; —CH$_2$CH$_2$CONH$_2$; —(CH$_2$)$_4$NH$_2$; —(CH$_2$)$_3$NHC(NH$_2$)$_2$;

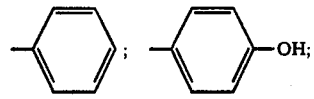

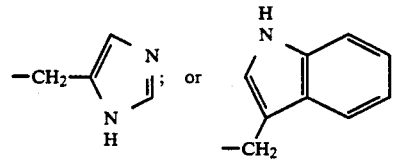

i. 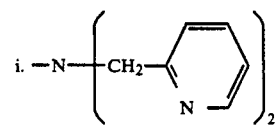

j. 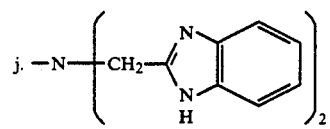

k. —NHC(O)CH$_2$N(CH$_2$COOH)CH$_2$CH$_2$N(CH$_2$COOH)$_2$
l. —NHC(O)CH$_2$N(CH$_2$COOH)CH$_2$CH$_2$N(CH$_2$COOH)CH$_2$CH$_2$N(CH$_2$COOH)$_2$
m. —N(CH$_2$COOH)CH$_2$CH$_2$N(CH$_2$COOH)$_2$.

n. 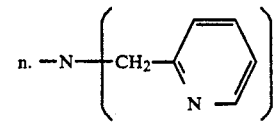

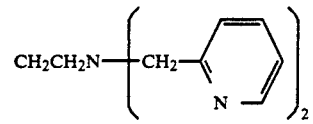

o. 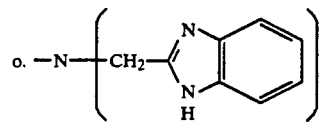

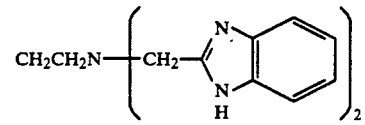

p. —YNHCH$_2$ĊH$_2$N(CH$_2$CH$_2$NH$_2$)$_2$
q. —YNHCH$_2$CH$_2$CH$_2$NHCH$_2$CH$_2$NHCH$_2$CH$_2$CH$_2$NH$_2$
r. —YNHCH$_2$CH$_2$NHCH$_2$CH$_2$NHCH$_2$CH$_2$NH$_2$ s. —YOCH$_2$CH$_2$N(CH$_2$COOH)CH$_2$CH$_2$N(CH$_2$COOH)$_2$ t. —YOCH[CH$_2$N(CH$_2$COOH)$_2$]$_2$ wherein Y in PEG- and PPG-based compounds is —NHC(O)CH$_2$CH$_2$C(O)— and in other compounds it is —C(O)— only.

The compounds which terminate with formula a, b, c, d, e, f, g or h can be prepared by reacting the corresponding amine with the alkyl halide or sulfonate, or X—P—X where X=Cl, Br, I, or OSO$_2$R.

The compounds which terminate with formula a, i or j can be prepared by reacting H$_2$N—P—NH$_2$ with the appropriate alkyl halide or sulfonate.

The compounds that terminate with formulas k or l can be prepared by reacting H$_2$N—P—NH$_2$ with the appropriate acid, via an activated form of the acid or with the assistance of a coupling agent.

The compounds that terminate with formula m, n or o can be prepared by reacting NH$_2$CH$_2$CH$_2$NH—P—NHCH$_2$CH$_2$NH$_2$ with the appropriate alkyl halide.

The compounds that terminate with formula p, q, r, s or t are prepared by reacting HOY—P—YOH with the appropriate amine or alcohol, via an activated form of the acid or with the assistance of a coupling agent.

Literature preparations are available for the PEG derivatives terminated with halides, amines, carboxylates and ethylene diamines.

Many dihalides, diamines, and diacids are commercially available, and can be used to make bis-chelates with a variety of properties.

The bis-chelates of lower molecular weight (less than 4,000) can be metallated by treating the chelate with one mole of the appropriate metal salt per mole of chelating group. The chelates of higher molecular weight (greater than about 4,000) can be metallated by dissolving the chelate in water with an excess of the metal salt, followed by exhaustive dialysis of the resulting solution against distilled water to remove the excess metal salt. Dialysis tubing with a molecular weight cutoff of 1,000 is used. The dialyzed solution is then removed from the tubing and lyophilized to recover the metallated chelate.

The reactions to prepare the chelates from four basic starting materials are summarized in the following figures. The P represents the polymeric backbone or the bridging group of the preceding discussion. A likely coordination number and, in some cases, a geometry, is suggested for the resulting chelate. The actual geometry of the complex and, in some cases, the coordination number, will depend upon the metal ion chelated.

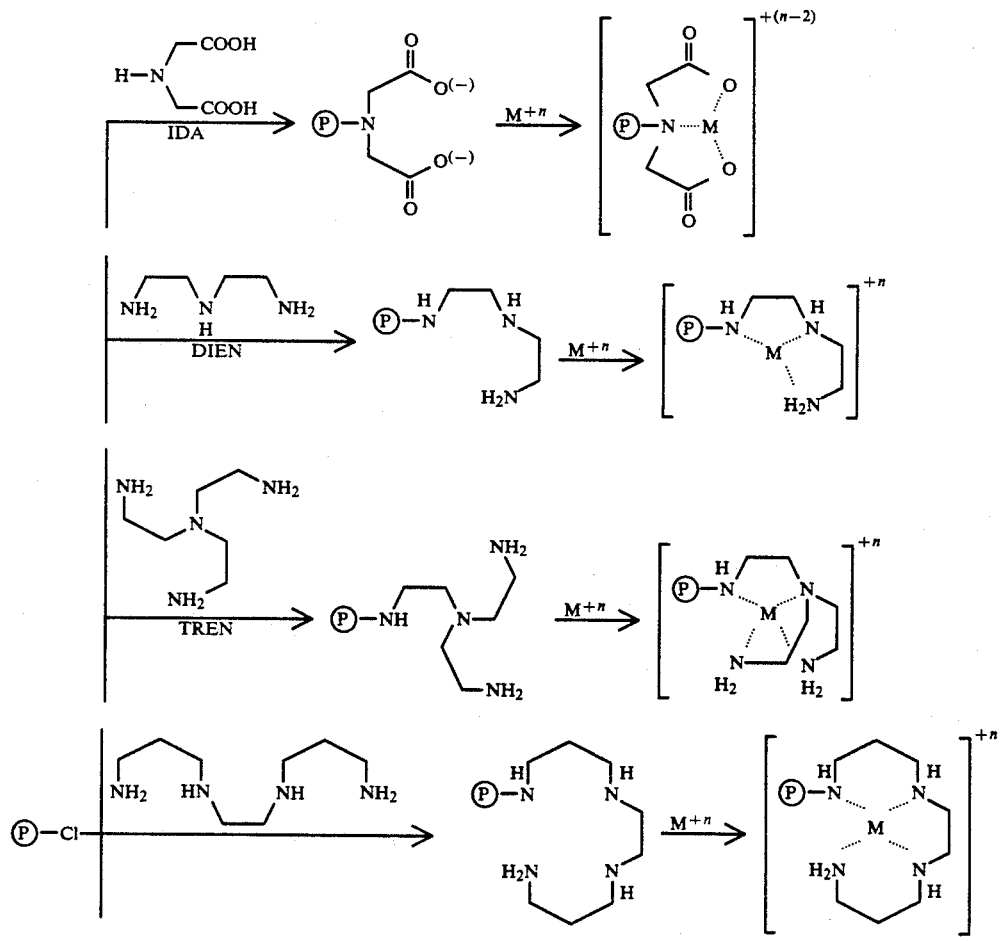

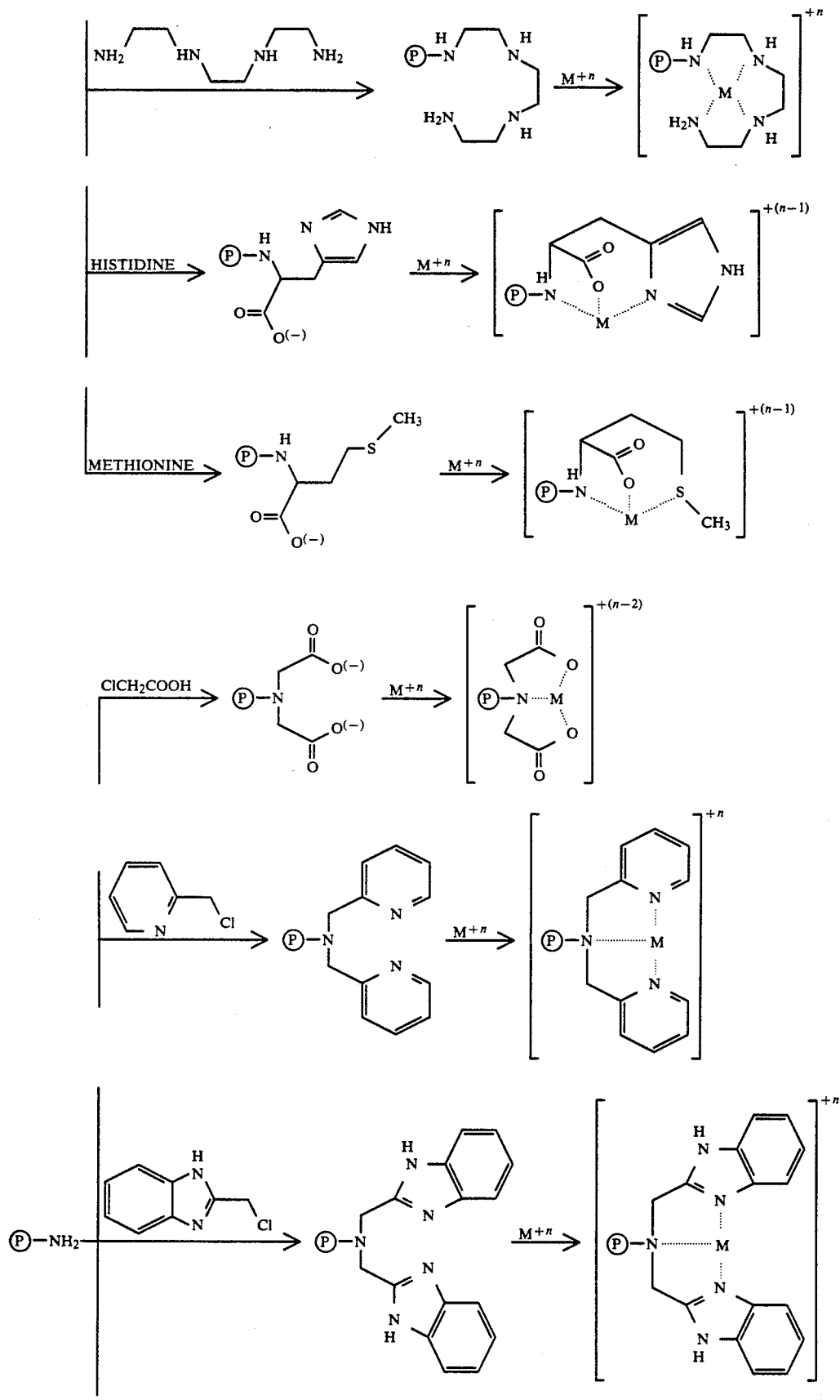

-continued
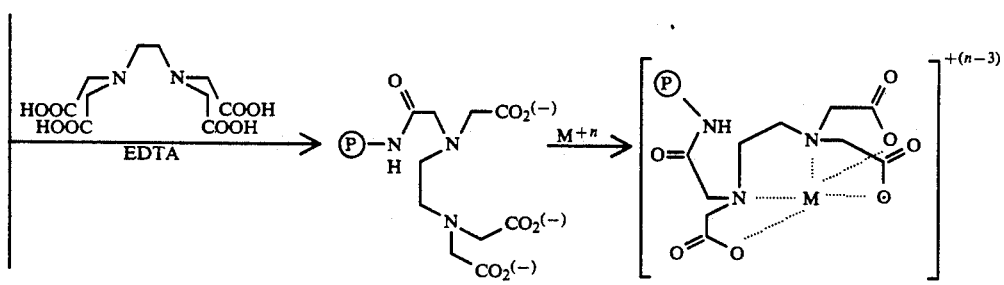
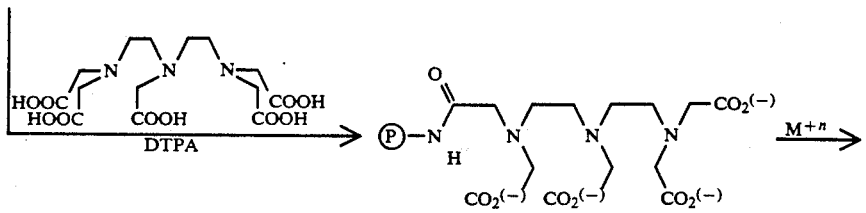
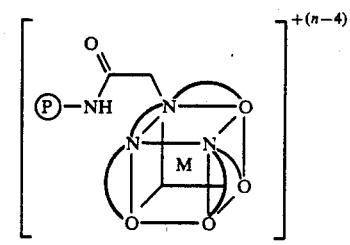
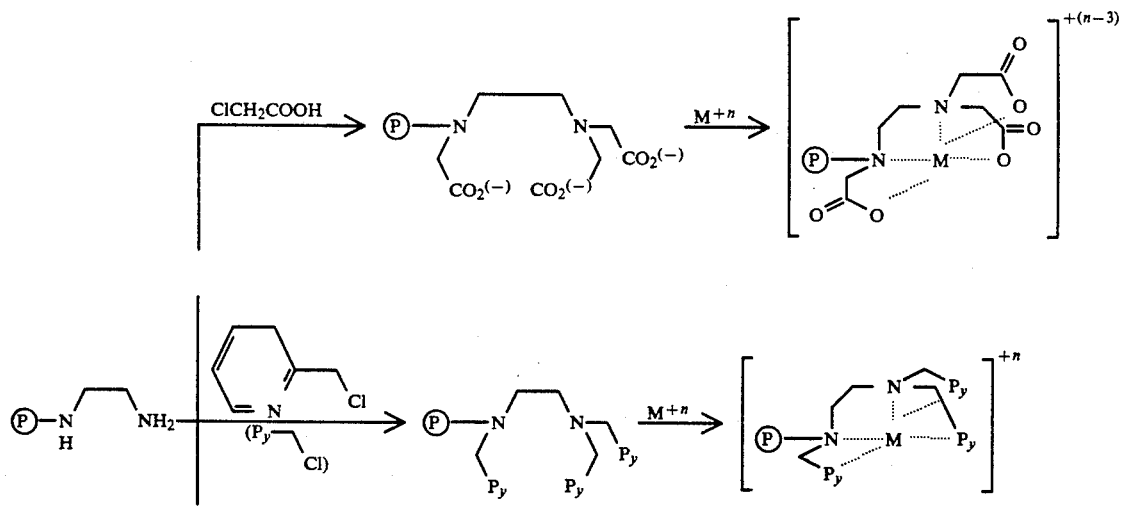
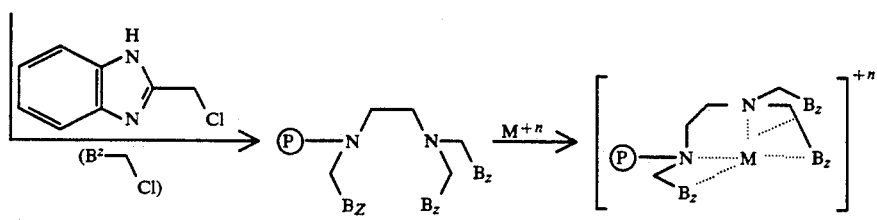

-continued

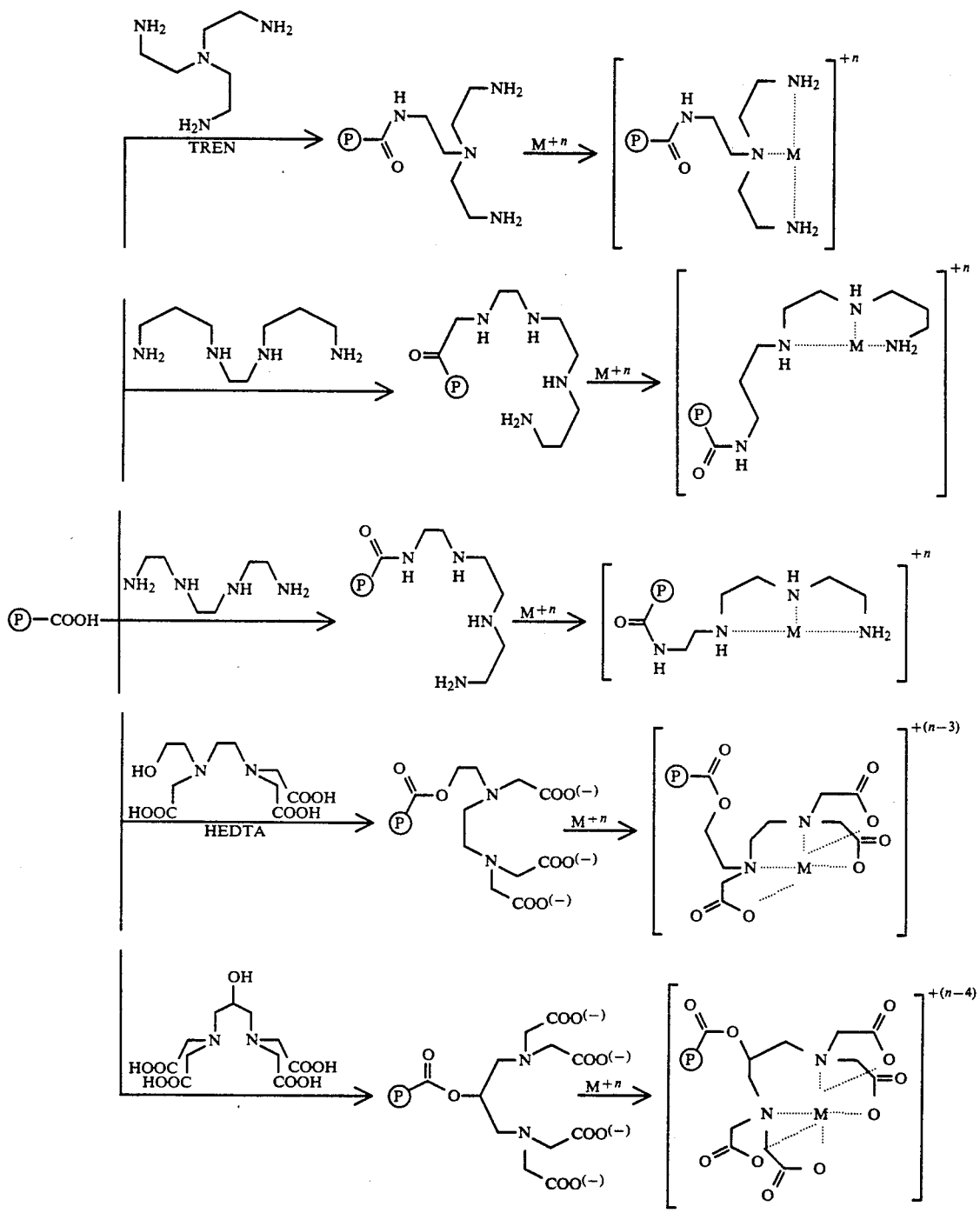

The proteins that are recoverable through this invention are those that bind immobilized metals. Proteins are known to interact with immobilized metal cations via amino acid side chains (e.g. histidine, cysteine, glutamic acid), phosphate groups, and amino groups on the N-terminus. The degree of interaction depends on the number and placement of these groups as well as the particular metal utilized in the separation. For example, a primary determinant of interactions with chelated copper cations is the number of surface-accessible histidine residues on the protein. On the other hand, chelated $Fe^{3+}$ is known to bind to phosphorylated proteins.

Numerous proteins are known to interact with immobilized metals in metal affinity chromatography. For example, the purification of the following proteins on specified metals has been reported and summarized by Sulkowski, E., *Protein Purifications: Micro to Macro*, pp. 149–162, Alan R. Liss (1987):

| Protein | Metal Ion |
| --- | --- |
| Human serum proteins | Zn, Cu, Ni |
| Lactoferrin | Cu |
| $a_2$-SH glycoprotein | Zn |
| Human fibroblast interferon | Zn |

-continued

| Protein | Metal Ion |
| --- | --- |
| a₂-macroglobulin | Zn |
| Plasminogen activator | Zn |
| Lysozyme | Cu |
| Nucleoside diphosphatase | Zn, Cu |
| Dolichos b. lectin | Ca |
| Non-histone proteins | Cu |
| Human serum albumin | Cu |
| Human fibrinogen | Zn |
| Phosphotyrosyl-protein phosphatase | Zn |
| Superoxide dismutase | Cu |
| Nitrate reductase | Zn |
| EGF, shrew | Ni |
| rMulFN— | Cu |
| Carboxypeptidases | Cu |
| Catalase | Cu |

Other proteins that can be purified by metal chelate separations include tissue plasminogen activator, urokinase and interleukin-1β.

Aqueous two-phase systems which may be used in the present extraction invention are well known in biological separations. For example, see *Partitioning in Aqueous Two-Phase Systems*, edited by H. Walter, D. E. Brooks, D. Fisher, Academic Press (1985) and *Partition of Cell Particles and Macromolecules*, P. Albertsson, Uppsala, 2nd edition (1971). Neither of these publications was concerned with extraction using metallated polymers.

A large number of aqueous multi-phase systems are described in *Partitioning in Aqueous Two-Phase Systems*, supra. The phase-forming materials may be polymeric materials or a single polymeric material in conjunction with an inorganic salt.

The multi-phase systems used in this invention will depend upon the protein which one wishes to partition and upon the other materials present in the mixture. Considerations in the selection of the multi-phase system include the molecular weight of the polymer, the weight percentage of the polymer or salt in the mixture, how much of the polymer is substituted with chelate, the properties of the protein to be extracted, the pH, and the properties of other components in the mixture.

In this invention, one of the polymer phases has been derivatized to contain chelated metal ions. Polyethylene glycol, for example, may be derivatized with iminodiacetic acid, and loaded with copper cations. It can be used in conjunction with a second polymer such as dextran or with inorganic salts to form an aqueous two-phase system.

Proteins that interact favorably with copper will partition with increased affinity into the PEG-Cu(II) phase. The protein is recovered by physical separation of the phases, followed by addition of acid or a competing ligand, such as free imidazole, to reduce the affinity of the protein for the metal. Following disruption of the protein-metal interaction, the formation of a new multiple-phase system can then be used to pull the protein into another phase, or the protein can be recovered from the metal-chelating polymer by other separation techniques such as chromatography, dialysis, or precipitation. The preferred metal-chelating polymers used in the extraction process are polyethylene glycol derivatives of average molecular weight from about 4,000 to about 100,000. They have been functionalized with metal-chelating groups and metal.

For the precipitation process, bis-metallated PEG or a small multi-metal chelate, such as ethylenebis(oxyethylenenitrilo)tetraacetic acid is added directly to the protein mixture whose pH has been adjusted to favor protein-metal binding. Mono-metal chelates may be employed for precipitation, but this usually requires that the metal chelate be present in approximately a tenfold molar excess relative to the protein to be precipitated. The mixture becomes turbid, and after sitting several hours, the protein precipitates. The protein can then be recovered from the precipitate by putting the precipitate into a solution with a lower pH, e.g., about 4, or by adding a competing ligand, such as free imidazole or EDTA.

The preferred systems for extraction are monofunctional metal-chelating PEGs—that is, PEGs substituted with metal chelating groups on one end only. The bis- and multi-functional compounds are preferred for the precipitation of proteins because of their ability to form large, insoluble complexes, which can be recovered by centrifugation.

NEW COMPOUNDS

Example 1

5 g MPEG5000-chloride (a monochloro derivative of PEG monomethyl ether having a molecular weight of about 5000), 2 g iminodiacetic acid (IDA) and 2 g potassium carbonate are dissolved in 50 mL distilled water and heated to reflux for 48 hours.

The solution is then transferred to a separatory funnel and mixed with 75 mL saturated sodium bicarbonate solution. This was extracted three times with 75 mL portions of dichloromethane. The combined dichloromethane solution was washed with 150 mL saturated sodium bicarbonate solution. 100 mL saturated KCl was added to aid the phase break.

The dichloromethane solution was removed and the aqueous phase was extracted twice with 50 mL portions of dichloromethane. The combined dichloromethane solution was washed again with 150 mL saturated bicarbonate and 100 mL saturated KCl as before. Finally, the combined dichloromethane solutions were washed with 200 mL of distilled water and made acidic with approximately 1 mL glacial acetic acid, giving a solution of about pH 5. After removing the lower phase, the upper phase was exhaustively extracted with four 100 mL portions of dichloromethane. The dichloromethane solutions were evaporated to dryness, and the residue was dissolved in a small amount of distilled water. This was then frozen and lyophilized to give a spongy product.

In an alternate workup, 5 g sodium sulfate was added to the reaction mixture after it had refluxed for 48 hours. This mixture separated into two phases in a separatory funnel. The lower phase, containing most of the sodium sulfate, excess iminodiacetic acid, and potassium carbonate, was discarded. The upper phase, containing most of the PEG-derivative, was transferred to dialysis tubing (MW 1000 cutoff), and dialysed for 4 hours against 0.1M sodium bicarbonate, and for 2 hours against distilled water. The solution then was removed from the dialysis tubing and lyophilized, giving the product as a spongy mass. This product had the PEG structure set out above with formula a as the ligands.

Copper (II) was then inserted into the resulting product by dissolving the product in a small amount of water in which a large (5×-10×) excess of copper sulfate had been dissolved. The resulting solution was next dialysed against distilled water for 5 hours to remove the excess copper sulfate. The solution was removed from the dialysis tubing and lyophilized, giving the metallated product as a blue spongy mass.

Example 2

5 g PEG-chloride (derived from (i.e., PEG-Cl$_2$ or α-chloroethyl)-ω-chloropolyoxyethylene, prepared from PEG having a molecular weight of about 8000 and another from MPEG-5000 which terminated at one end by a methoxy group; i.e. MPEG-chloride prepared from PGE monomethyl ether having a molecular weight of about 5000, was dissolved in 50 mL toluene and 0.5 mL NH$_2$CH$_2$CH$_2$—NHCH$_2$CH$_2$NH$_2$ was added to each (about a 3-fold excess in the case of the PEG-8000 and twice that in the case of the MPEG-5000). The reaction vessels were fitted with reflux condensers equipped with a drying tube and the mixture refluxed for 48 hours.

The reaction mixtures were evaporated to a small volume, and the residues redissolved in 50 mL saturated sodium bicarbonate solution. These solutions were transferred to separatory funnels and extracted several times with 50 mL to 100 mL portions of dichloromethane. The aqueous phases were discarded and the organic phases were washed twice with saturated sodium bicarbonate solution.

The dichloromethane was then evaporated to an oil on a rotary evaporator. Each oil was dissolved in a small amount of distilled water and lyophilized. The products were each a spongy mass. They corresponded to the general formula wherein A and B were formula b endings in the case of the PEG-8000 compound, and, in the case of the PEG-5000 compound, A was a formula b ending and B was methoxy.

These compounds could be metallated by the process used in Example 1.

Example 3

The process of Example 2 was repeated, substituting N(CH$_2$CH$_2$NH$_2$)$_3$ (TREN) for the amine. The resultant products correspond to the general formula wherein A and B were formula c endings on the PEG-8000 backbone and A was formula c and B was methoxy on the PEG-5000 backbone. These compounds also can be metallated by the process in Example 1.

Example 4

5.04 g of MPEG-chloride (derived from MPEG-5000, i.e., a monochloro derivative of a PEG monomethyl ether prepared from PEG monomethyl ether having a molecular weight of about 5000, 0.82 g of L-aspartic acid and 2.00 g of anhydrous potassium carbonate were dissolved in 45 mL of distilled water and refluxed for 67 hours. 3.5 g of anhydrous sodium sulfate was dissolved in the reaction mixture, which then separated into two phases. The phases were separated and the upper phase was exhaustively dialysed against distilled water to remove all low-molecular weight components. The dialysed solution was lyophilized to give the product corresponding to the general formula, wherein A was —NHCH(CH$_2$COOH)COOH and B was methoxy. The compound was metallated by the process used in Example 1.

Example 5

The process of Example 4 was repeated, substituting D-aspartic acid for the L-isomer. The compound was metallated by the process used in Example 1.

Example 6

5.46 g of PEG-chloride (derived from MPEG-5000), 0.86 g of L-methionine and 0.84 of anhydrous potassium carbonate were dissolved in 40 mL of distilled water and refluxed for 96 hours. 7.0 g of anhydrous sodium sulfate was dissolved in the reaction mixture, which then separated into two phases. The phases were separated and the upper phase was exhaustively dialysed against distilled water to remove all low-molecular weight components. The dialysed solution was lyophilized to give the product corresponding to the general formula, wherein A was —NHCH(CH$_2$CH$_2$SCH$_3$)COOH and B was methoxy. The compound was metallated by the process used in Example 1.

Example 7

The process of Example 6 was repeated, substituting D-methionine for the L-isomer. The compound was metallated by the process used in Example 1.

EXTRACTION OF PROTEINS

Example 8

Partitioning of protein was carried out as follows: a two-phase system, hereinafter called System A, was formulated in a 15 cc centrifuge tube. 1.30 g of a 13.5 wt. % solution of dextran (T500), 0.70 g of a solution made up of 40% (w/w) monomethylether PEG, average molecular weight 5000, and containing 0.4% (w/w) Cu(II)-MPEG5000-Iminodiacetic acid, 1.0 g of 0.04M sodium phosphate pH 8.0, and 1.0 g protein solution (1.0 mg/g in 0.4M NaCl).

The partition coefficients (ratio of the protein in the top [PEG] phase to that in the bottom phase) and percentage of protein recovered in the top phase are:

| Protein | Partition Coefficient | Recovery |
|---|---|---|
| Sperm whale myoglobin | 0.85 | 73% |
| Bovine hemoglobin | 13 | 97% |

Example 9

PEG/dextran two-phase systems were made by combining 1.30 g of a 13.5% (w/w) dextran solution, 0.70 g of a 40% (w/w) PEG4000 solution, 1.0 g of 0.04M sodium phosphate and 1.0 mg/g protein in 0.4M NaCl. When Cu(II)PEG-IDA was used, it represented 1% of the total PEG added, or roughly 0.06% of the hydroxyl groups substituted with chelated copper. Partition coefficients for heme-containing proteins in PEG/dextran (K$_0$) and Cu(II) PEG-IDA/dextran (K) two-phase systems at different pHs are set out below.

| Proteins | pH 8.0 | | pH 7.0 | | pH 5.5 | |
|---|---|---|---|---|---|---|
| | K$_O$ | K | K$_O$ | K | K$_O$ | K |
| cytochromes c | | | | | | |
| tuna | 0.48 | 0.46 | 0.56 | 0.53 | — | — |
| horse | 0.41 | 0.39 | — | — | — | — |
| c. krusei | 0.56 | 0.75 | 0.59 | 0.72 | — | — |
| myoglobins | | | | | | |
| horse | 0.36 | 0.64 | 0.37 | 0.51 | — | — |
| whale | 0.42 | 0.85 | 0.40 | 0.73 | 0.45 | 0.50 |
| hemoglobins | | | | | | |
| turkey | 0.25 | 4.8 | 0.30 | 1.6 | — | — |
| cow | 0.25 | 6.0 | 0.25 | 1.8 | 0.34 | 0.45 |
| horse | 0.25 | 7.2 | — | — | — | — |

-continued

| Proteins | pH 8.0 | | pH 7.0 | | pH 5.5 | |
|---|---|---|---|---|---|---|
| | $K_O$ | K | $K_O$ | K | $K_O$ | K |
| human | 0.38 | 14 | 0.35 | 3.4 | 0.46 | 0.63 | sults, set out below, demonstrate that the partition coefficient for a given protein can be significantly altered by both the type of chelate used and by the chirality of the chelate. This allows the design of systems which can separate proteins of similar bulk properties and number of surface-accessible histidines.

TABLE 1

Results of the protein partition coefficient measurements for the five PEG-derivatized metal chelates studied. Each $K_o$ and $K_p$ value is an average of several measurements, typically 6 to 8, and ranging from 5 to 14 measurements.

| Exposed Histidines | | Tuna Cyt c 0 | C. krusei Cyt c 2 | Horse Mb 4 | Sheep Mb 5 | Whale Mb 5 |
|---|---|---|---|---|---|---|
| $K_o \pm \sigma^*$ | | 0.48 ± 2.9% | 0.58 ± 2.4% | 0.39 ± 3.6% | 0.38 ± 2.9% | 0.47 ± 3.0% |
| $K_p \pm \sigma^*$ | IDA | 0.52 ± 1.7% | 0.83 ± 2.6% | 0.75 ± 3.3% | 1.10 ± 3.5% | 0.97 ± 1.7% |
| | L-Asp | 0.49 ± 2.9% | 0.72 ± 4.6% | 0.53 ± 0.8% | 0.52 ± 5.3% | 0.60 ± 1.4% |
| | D-Asp | 0.47 ± 1.1% | 0.68 ± 2.7% | 0.54 ± 2.2% | 0.50 ± 4.0% | 0.53 ± 1.2% |
| | L-Met | 0.49 ± 3.3% | 0.75 ± 2.7% | 0.73 ± 1.6% | 0.73 ± 4.0% | 0.55 ± 1.8% |
| | D-Met | 0.49 ± 3.3% | 0.74 ± 3.6% | 0.49 ± 3.8% | 0.49 ± 1.6% | 0.53 ± 1.9% |
| $\ln(K_p/K_o)$ | IDA | 0.065 | 0.36 | 0.66 | 1.07 | 0.73 |
| | L-Asp | 0.020 | 0.20 | 0.32 | 0.32 | 0.25 |
| | D-Asp | −0.017 | 0.15 | 0.33 | 0.28 | 0.13 |
| | L-Met | 0.023 | 0.26 | 0.64 | 0.66 | 0.17 |
| | D-Met | 0.017 | 0.23 | 0.24 | 0.27 | 0.12 |

*The standard deviation of each partition coefficient is given as a percentage of the mean value.

Example 10

An aqueous two-phase system was made from the following components: 1.5 g of 40% MPEG5000 (PEG monomethyl ether) containing 0.4% Cu(II) MPEG-IDA, 0.30 g anhydrous sodium sulfate, 1.06 g water, and 1.0 g of a solution of protein (1.0 mg/g) in 0.04M sodium phosphate pH 8.0. The partition coefficients for various proteins are listed below.

| Protein | Partition Coefficient |
|---|---|
| c. krusei cytochrome c | 0.03 |
| whale myoglobin | 0.04 |
| turkey hemoglobin | 3.4 |
| bovine hemoglobin | 4.9 |
| human hemoglobin | 80. |

Example 11

The top PEG phase from system A containing 1.0 mg bovine hemoglobin was withdrawn from the 15 cc tube in Example 8 for recovery of the protein contained therein. To 2.7 g of top phase was added 0.60 g anhydrous sodium sulfate, two drops of weak HCl to lower the pH to 5.5, and water to a final weight of 5.2 g. Upon separation of the phases, 90% of the bovine hemoglobin was recovered in the bottom, sodium sulfate, phase. This example demonstrates the recovery of protein extracted into the PEG-metal chelate.

Example 12

4.00 g PEG/dextran two-phase systems were prepared so that the final systems contained 4.4% (w/w) dextran, 1 mg total protein being extracted, and 7% (w/w) total PEG. When a metallated PEG was used, the amount was adjusted to make the copper concentration $9.8 \times 10^{-4}$% (w/w). The remainder of the PEG was unsubstituted MPEG-5000.

Such systems were prepared using PEG containing no metal chelate and containing the PEG-substituted metal chelates of Examples 1, 4, 5, 6, and 7. Five proteins—tuna cytochrome c, C. krusei cytochrome c, horse myoglobin, sheep myoglobin, and whale myoglobin—were partitioned using these systems. The re-

PRECIPITATION

Example 13

PEG-tren-Cu(II), average molecular weight 8000, was made as described in Example 3. 2.1 mg of this compound was added to 1.0 mL of 0.04M sodium phosphate pH 8.0 containing 1.0 mg of human hemoglobin. After 18 hours at room temperature, 97% of the hemoglobin had precipitated. The precipitate can be recovered by centrifugation. After decanting the supernatant, the precipitate is dissolved in a solution containing EDTA.

Example 14

2.23 mg of PEG-tren-Cu(II), prepared in Example 3, was added to 1.2 mL solution containing two proteins, human hemoglobin (0.83 mg/mL) and horse heart cytochrome c (0.83 mg/mL). The solution also contained 0.033M sodium phosphate pH 8.0 and 0.07M NaCl. After 24 hours, 100% of the hemoglobin had precipitated and could be recovered in insoluble form by centrifugation. The horse heart cytochrome c, which is known not to interact strongly with immobilized metals, was quantitatively recovered in the supernatant.

This example shows the selectivity of the precipitation. Only proteins with a large affinity for the immobilized metal will form insoluble complexes, while those that do not interact with the metal remain soluble.

Example 15

Ethylenebis(oxyethylenenitrilo)tetraacetic acid (EGTA) is commercially available. 71.8 mg were dissolved with 91.4 mg $CuSO_4$ in 36.6 mL of water. 30 microliters of this solution was added to 1.17 mL of sodium phosphate pH 8.0 containing 1 mg of human hemoglobin. After 12 hours 99% of the hemoglobin had precipitated. This example demonstrates the use of small (nonpolymeric) bivalent metal chelates of $CuSO_4$ does not induce the same high degree of precipitation.

INDUSTRIAL APPLICABILITY

The processes and novel compounds described and claimed herein can be used to recover selectively valuable proteins from mixtures or to remove selectively harmful proteins from such mixtures.

We claim:

1. A compound of the formula:

wherein R is H or $CH_3$, A is a chelating group and B is a chelating group, $OCH_3$ or OH, said compound being metallated with a metal ion selected from the group consisting of $Cu^{2+}$, $Zn^{2+}$, $Ni^{2+}$, $Fe^{3+}$, $Fe^{2+}$, $Co^{2+}$, $Ca^{2+}$, $Cd^{2+}$ and $Hg^{2+}$ and wherein n is chosen so that the compound has a molecular weight prior to metallation between about 1500 to about 20,000.

2. A compound of claim 1 wherein A is selected from the following:
   a. $-N(CH_2COOH)_2$
   b. $-NHCH_2CH_2NHCH_2CH_2NH_2$
   c. $-NHCH_2CH_2N(CH_2CH_2NH_2)_2$
   d. $-NHCH_2CH_2CH_2NHCH_2CH_2NHCH_2CH_2CH_2NH_2$
   e. $-NHCH_2CH_2NHCH_2CH_2NHCH_2CH_2NH_2$
   f. 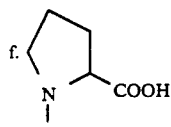
   g. $-NHCH(X)COOH$ (D- or L-amino acids)
   h. $-N(CH_2COOH)CH(X)COOH$ [D- or L- N-(carboxymethyl)amino acids]; wherein X in g and h is $-H$; $-CH_3$; $-CH(CH_3)_2$; $-CH_2CH(CH_3)_2$; $-CH(CH_3)CH_2CH_3$; $-CH_2CH_2SCH_3$; $-CH_2OH$; $-CH(OH)CH_3$; $-CH_2SH$; $-CH_2COOH$; $-CH_2CONH_2$; $-CH_2CH_2COOH$; $-CH_2CH_2CONH_2$; $-(CH_2)_4NH_2$; $-(CH_2)_3NHC(NH_2)_2$;

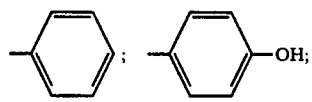

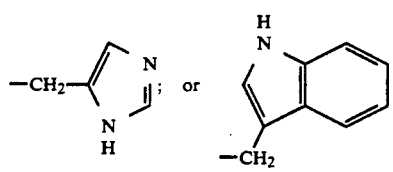

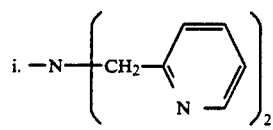

j. 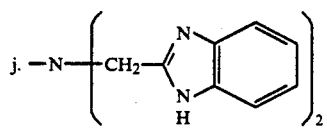

k. $-NHC(O)CH_2N(CH_2COOH)CH_2CH_2N(CH_2COOH)_2$
l. $-NHC(O)CH_2N(CH_2COOH)CH_2CH_2N(CH_2COOH)CH_2CH_2N(CH_2COOH)_2$
m. $-N(CH_2COOH)CH_2CH_2N(CH_2COOH)_2$.

n. 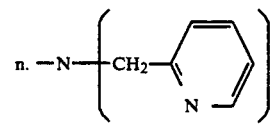

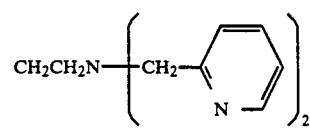

o. 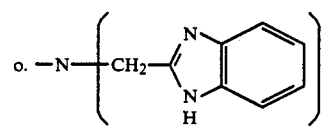

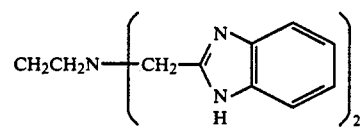

p. $-YNHCH_2CH_2N(CH_2CH_2NH_2)_2$
q. $-YNHCH_2CH_2CH_2NHCH_2CH_2NHCH_2CH_2CH_2NH_2$
r. $-YNHCH_2CH_2NHCH_2CH_2NHCH_2CH_2NH_2$
s. $-YOCH_2CH_2N(CH_2COOH)CH_2CH_2N(CH_2COOH)_2$
t. $-YOCH[CH_2N(CH_2COOH)_2]_2$ wherein Y in PEG- and PPG-based compounds is $-NHC(O)CH_2CH_2C(O)-$ and in other compounds it is $-C(O)-$ only; and B is selected from a to t, $OCH_3$, or OH.

3. A compound of claim 1 wherein R is H.
4. A compound of claim 1 where R is $CH_3$.
5. A compound of claim 1 wherein A and B are the same.
6. A compound of the formula:

wherein A is a chelating group and B is a chelating group, $OCH_3$ or OH, said compound being metallated with a metal ion selected from the group consisting of $Cu^{2+}$, $Zn^{2+}$, $Ni^{2+}$, $Fe^{3+}$, $Fe^{2+}$, $Co^{2+}$, $Ca^{2+}$, $Cd^{2+}$ and $Hg^{2+}$ and wherein n is chosen so that the compound has a molecular weight prior to metallation of between about 1500 to 20,000.

7. A compound of claim 6 wherein A is selected from:
   a. $-N(CH_2COOH)_2$ b. —NHCH$_2$CH$_2$NHCH$_2$CH$_2$NH$_2$
c. —NHCH$_2$CH$_2$N(CH$_2$CH$_2$NH$_2$)$_2$
d. —NHCH$_2$CH$_2$CH$_2$NHCH$_2$CH$_2$NHCH$_2$CH$_2$-NH$_2$
e. —NHCH$_2$CH$_2$NHCH$_2$CH$_2$NHCH$_2$CH$_2$NH$_2$

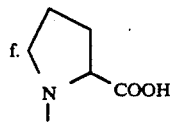
f.

g. —NHCH(X)COOH (D- or L-amino acids)
h. —N(CH$_2$COOH)CH(X)COOH [D- or L- N-(carboxymethyl)amino acids]; wherein X in g and h is —H; —CH$_3$; —CH(CH$_3$)$_2$; —CH$_2$CH(CH$_3$)$_2$; —CH(CH$_3$)CH$_2$CH$_3$; —CH$_2$CH$_2$SCH$_3$; —CH$_2$OH; —CH(OH)CH$_3$; —CH$_2$SH; —CH$_2$COOH;

—CH$_2$CONH$_2$; —CH$_2$CH$_2$COOH; —CH$_2$CH$_2$CONH$_2$; —(CH$_2$)$_4$NH$_2$; —(CH$_2$)$_3$NHC(NH$_2$)$_2$;

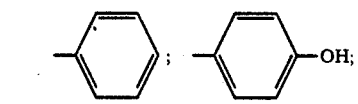

8. A compound of claim 6 wherein A and B are the same.

9. A compound of claim 7 wherein A and B are each a.

* * * * *